United States Patent
Day et al.

(10) Patent No.: US 9,870,492 B2
(45) Date of Patent: Jan. 16, 2018

(54) METHOD AND SYSTEM FOR DETERMINING INFORMATION RELATED TO A DRUG RESERVOIR

(75) Inventors: Shane Alistair Day, Warwickshire (GB); Barry Yates, Warwickshire (GB); Richard James Vincent Avery, Gloucestershire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 429 days.

(21) Appl. No.: 13/522,489

(22) PCT Filed: Jan. 21, 2011

(86) PCT No.: PCT/EP2011/050797
§ 371 (c)(1),
(2), (4) Date: Dec. 4, 2012

(87) PCT Pub. No.: WO2011/089205
PCT Pub. Date: Jul. 28, 2011

(65) Prior Publication Data
US 2013/0072897 A1    Mar. 21, 2013

Related U.S. Application Data

(60) Provisional application No. 61/297,606, filed on Jan. 22, 2010.

(30) Foreign Application Priority Data

Apr. 23, 2010  (EP) .................................... 10160865

(51) Int. Cl.
*A61M 5/00*   (2006.01)
*G06K 7/10*   (2006.01)
(Continued)

(52) U.S. Cl.
CPC ................ *G06K 7/10* (2013.01); *A61M 5/00* (2013.01); *A61M 5/24* (2013.01);
(Continued)

(58) Field of Classification Search
CPC .. A61M 2205/6081; A61M 2205/6009; A61M 2205/6063; A61M 2205/27; A61M 2205/276
(Continued)

(56) References Cited

U.S. PATENT DOCUMENTS 533,575 A     2/1895  Wilkens
5,226,895 A   7/1993  Harris
(Continued)

FOREIGN PATENT DOCUMENTS

EP   0341799   11/1989
EP   0937471    8/1999
(Continued)

OTHER PUBLICATIONS

Notification of Reasons for Refusal for Japanese App. No. 2012-549363, dated Nov. 4, 2014.
(Continued)

*Primary Examiner* — Theodore Stigell
*Assistant Examiner* — Benjamin Koo
(74) *Attorney, Agent, or Firm* — McDonnell Boehnen Hulbert & Berghoff LLP

(57) ABSTRACT

A method and system for detecting information related to a drug reservoir. The method includes transmitting energy at a coded material disposed on a drug reservoir, where the energy has at least one predefined characteristic. The coded material identifies information related to the drug reservoir. The coded material modifies the energy and emits the modified energy to a receiver. The method further includes receiving at the receiver the modified energy. The method (Continued)

further includes determining information related to the drug reservoir based on the modified energy as the drug reservoir is loaded into a drug delivery device.

14 Claims, 7 Drawing Sheets

(51) Int. Cl.
- *A61M 5/24* (2006.01)
- *G06K 7/12* (2006.01)
- *G06K 19/06* (2006.01)
- *G06F 19/00* (2011.01)
- *A61M 5/145* (2006.01)
- *A61M 5/20* (2006.01)
- *A61M 5/315* (2006.01)
- *A61M 5/48* (2006.01)
- *A61M 15/00* (2006.01)
- *A61M 5/31* (2006.01)

(52) U.S. Cl.
CPC ......... *G06F 19/3468* (2013.01); *G06K 7/12* (2013.01); *G06K 19/06037* (2013.01); *A61M 5/1452* (2013.01); *A61M 5/20* (2013.01); *A61M 5/2425* (2013.01); *A61M 5/31525* (2013.01); *A61M 5/31546* (2013.01); *A61M 5/31583* (2013.01); *A61M 5/482* (2013.01); *A61M 15/008* (2014.02); *A61M 15/0065* (2013.01); *A61M 15/0068* (2014.02); *A61M 15/0081* (2014.02); *A61M 15/0083* (2014.02); *A61M 2005/2407* (2013.01); *A61M 2005/2496* (2013.01); *A61M 2005/3125* (2013.01); *A61M 2205/12* (2013.01); *A61M 2205/18* (2013.01); *A61M 2205/27* (2013.01); *A61M 2205/276* (2013.01); *A61M 2205/43* (2013.01); *A61M 2205/44* (2013.01); *A61M 2205/50* (2013.01); *A61M 2205/52* (2013.01); *A61M 2205/6009* (2013.01); *A61M 2205/6063* (2013.01); *A61M 2205/6081* (2013.01)

(58) Field of Classification Search
USPC .......................................... 604/500; 235/375
See application file for complete search history.

(56) References Cited

U.S. PATENT DOCUMENTS

| | | | |
|---|---|---|---|
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 2001/0034506 A1* | 10/2001 | Hirschman | A61M 5/14546 604/207 |
| 2002/0032429 A1* | 3/2002 | Hjertman et al. | 604/500 |
| 2002/0038392 A1* | 3/2002 | De La Huerga | 710/8 |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2006/0224128 A1* | 10/2006 | Lurvey | A61M 5/14228 604/250 |
| 2007/0167919 A1* | 7/2007 | Nemoto | A61M 5/007 604/189 |
| 2008/0084276 A1* | 4/2008 | Bauchot | G06K 19/0672 340/10.1 |
| 2009/0275916 A1 | 11/2009 | Harms et al. | |
| 2012/0330228 A1* | 12/2012 | Day | A61M 5/14244 604/82 |

FOREIGN PATENT DOCUMENTS

| | | |
|---|---|---|
| EP | 0937476 | 8/1999 |
| GB | 2263068 | 7/1993 |
| JP | 2000-513967 | 10/2000 |
| JP | 2006-314815 | 11/2006 |
| JP | 2009-534080 | 9/2009 |
| WO | 96/14043 | 5/1996 |
| WO | 98/00187 | 1/1998 |
| WO | 99/38554 | 8/1999 |
| WO | 01/10484 | 2/2001 |
| WO | 2006/084464 | 8/2006 |
| WO | 2006/129301 | 12/2006 |
| WO | 2007/122473 | 11/2007 |

OTHER PUBLICATIONS

International Preliminary Report on Patentability for Int. App. No. PCT/EP2011/050794, dated Aug. 2, 2012.
International Search Report for Int. App. No. PCT/EP2011/050797, completed Jul. 6, 2011.

* cited by examiner

METHOD AND SYSTEM FOR DETERMINING INFORMATION RELATED TO A DRUG RESERVOIR

CROSS REFERENCE TO RELATED APPLICATIONS

The present application is a U.S. National Phase Application pursuant to 35 U.S.C. §371 of International Application No. PCT/EP2011/050797 filed Jan. 21, 2011, which claims priority to U.S. Provisional Patent Application No. 61/297,606 filed on Jan. 22, 2010 and European Patent Application No. 10160865.1 filed Apr. 23, 2010. The entire disclosure contents of these applications are herewith incorporated by reference into the present application.

FIELD OF THE INVENTION

The present disclosure is generally directed to a method and system for determining information related to a drug reservoir, particularly a drug reservoir containing a medicament. As just one example, such medicament reservoirs may comprise an ampoule, a cartridge, or a vial and may be used with a medical delivery device. Such exemplary medical delivery devices could comprise a syringe, a pen type syringe, a pump, or other similar device that requires a reservoir containing at least one medicament.

BACKGROUND

The present disclosure is generally directed to reservoirs, particularly reservoirs containing a medicament. More particularly, the present disclosure is generally directed to determining information related to a drug reservoir, which may help ensure that a drug delivery device can only be used with a drug reservoir for which it is intended. As just one example, such medicament reservoirs may comprise an ampoule, a cartridge, a vial, or a pouch, and may be used with a medical delivery device. Exemplary medical delivery devices include, but are not limited to syringes, pen type injection syringes, pumps, inhalers, or other similar injection or infusing devices that require at least one reservoir containing at least one medicament.

Medicament reservoirs such as ampoules, cartridges, or vials are generally known. Such reservoirs are especially used for medicaments that may be self administered by a patient. For example, with respect to insulin, a patient suffering from diabetes may require a certain amount of insulin to either be injected via a pen type injection syringe or infused via a pump. With respect to certain known reusable pen type drug delivery devices, a patient loads a cartridge containing the insulin into a proximal end of a cartridge holder. After the cartridge has been correctly loaded, the user may then be called upon to select a dose of medicament. Multiple doses may be dosed from the cartridge. Where the drug delivery device comprises a reusable device, once the cartridge is empty, the cartridge holder may be disconnected from the drug delivery device and the empty cartridge may be removed and replaced with a new cartridge. Most suppliers of such cartridges recommend that the user dispose of the empty cartridges properly. Where the drug delivery device comprises a disposable device, once the cartridge is empty, the user is recommended to dispose of the entire device.

Such known self administration systems requiring the removal and reloading of empty cartridges have certain limitations. For example, in certain generally known systems, a user simply loads a new cartridge into the delivery system without the drug delivery device or without the cartridge having any mechanism of preventing cross use of an incorrect cartridge. That is, the drug delivery device does not have a mechanism for determining if the medicament contained in the cartridge is indeed the correct type of medicament to be administered by the patient. Alternatively, certain known drug delivery devices do not present a mechanism for determining if the correct type of medicament within the cartridge should be used with that particular drug delivery system. This potential problem could be exacerbated given that certain elderly patients, such as those suffering from diabetes, may have limited manual dexterity. Identifying an incorrect medicament is quite important, since the administration of a potentially incorrect dose of a medicament such as a short acting insulin in lieu of a long insulin could result in injury or even death.

Some drug delivery devices or systems may use a color coding scheme to assist a user or care giver in selecting the correct cartridge to be used with a drug delivery device. However, such color coding schemes pose challenges to certain users, especially those users suffering from poor eyesight or color blindness: a situation that can be quite prevalent in patients suffering from diabetes.

Another concern that may arise with such disposable cartridges is that these cartridges are manufactured in essentially standard sizes and manufactured to comply with certain recognized local and international standards. Consequently, such cartridges are typically supplied in standard sized cartridges (e.g., 3 ml cartridges). Therefore, there may be a variety of cartridges supplied by a number of different suppliers and containing a different medicament, but they may fit a single drug delivery device. As just one example, a first cartridge containing a first medicament from a first supplier may fit a medical delivery device provided by a second supplier. As such, a user might be able to load and then dispense an incorrect medicament (such as a rapid or basal type of insulin) into a drug delivery device without being aware that the medical delivery device was perhaps neither designed nor intended to be used with such a cartridge.

As such, there is a growing desire from users, health care providers, care givers, regulatory entities, and medical device suppliers to reduce the potential risk of a user loading an incorrect drug type into a drug delivery device. There is also, therefore, a desire to reduce the risk of dispensing an incorrect medicament (or the wrong concentration of the medicament) from such a drug delivery device.

The problem to be solved by the present invention is to provide a drug reservoir and a drug delivery system where the safety for the user is improved.

SUMMARY

According to an exemplary embodiment, a method of determining information related to a drug reservoir may comprise receiving energy, for example electromagnetic radiation, from a coded material. The coded material may be disposed on a drug reservoir and may identify information related to the drug reservoir. As an example, the information may be selected from the group comprising drug type, drug concentration, a manufacturing date of the reservoir, an expiration of the drug and a storage condition of the drug. Electronic means for determining the information may be provided. The electronic means may comprise a receiver for receiving the energy emitted by the coded material. The receiver may comprise at least one photosensor. Based on the received energy, as an example based on the received electromagnetic radiation, the information identified by the coded material may be determined. Furthermore, the electronic means may comprise a transmitter for transmitting electromagnetic radiation to the coded material. The transmitter may comprise an LED.

The method may comprise, before receiving energy emitted by the coded material, the step of transmitting energy at the coded material. The coded material, which identifies information related to the drug reservoir, may modify the energy, for example the electromagnetic radiation, and then emit the modified energy, for example the modified electromagnetic radiation, to the receiver. The transmitted energy may have at least one predefined characteristic, which may be modified by the coded material. In particular, the coded material may modifiy the energy, for example the electromagnetic radiation, by at least one of (i) shifting the frequency of the transmitted radiation, (ii) filtering the radiation, (iii) absorbing the transmitted radiation followed by gradually releasing the radiation, (iv) absorbing the transmitted radiation followed by releasing the radiation after a given delay, and (v) shifting the phase of the transmitted radiation. The method may further include receiving the modified energy at the receiver and, based on this modified energy, for example based on the modified characteristic, determine information related to the drug reservoir.

According to a first specific embodiment, a method of determining information related to a drug reservoir comprises an electronic means detecting light energy from a coded material. The coded material is disposed on the drug reservoir, and this coded material comprises material having at least one color. The method may further include determining the color of the detected light or light energy. Based on the color of the detected light or light energy, information related to the drug reservoir may be determined.

According to a second specific embodiment, a method of determining information related to a drug reservoir comprises transmitting energy at a coded material disposed on a drug reservoir, wherein the energy has at least one predefined characteristic and wherein the coded material identifies information related to the drug reservoir. The coded material modifies the energy and emits the modified energy to a receiver. Based on the modified energy, information related to the drug reservoir is determined.

According to a further specific embodiment, a method of determining information related to a drug reservoir comprises providing a drug reservoir comprising a coded material, wherein the coded material identifies information related to the drug reservoir. The method further comprises providing electronic means for determining the information, wherein the electronic means comprise a receiver and receiving by the receiver electromagnetic radiation emitted from the coded material. Based on the received electromagnetic radiation, information identified by the coded material is determined.

As an example, the step of determining information may be performed as the drug reservoir is loaded into the drug delivery device. Here, it may be determined that the drug reservoir is not intended for use with the drug delivery device. Then, an insertion of the drug reservoir into the drug delivery device may be prevented, for example by activating an electronic latch. Additionally or alternatively, an indication that the drug reservoir is not intended for use with the rug delivery device may be displayed.

According to another exemplary embodiment, a medical delivery device may comprise a drug reservoir holder operable to receive a drug reservoir. The delivery device may further comprise electronic means, for example an electronic device, for detecting information related to the drug reservoir. The electronic means may comprise a transmitter configured to transmit energy. Furthermore, the electronic means may comprise a receiver configured to receive energy. Moreover, the delivery device may comprise a processor and data storage. The processor may be configured to execute or trigger steps of determining information and execute or trigger actions based on the determined information. The data storage may comprise instructions executable by the processor to based upon the received electromagnetic radiation determine the information related to the drug reservoir. Additionally or alternatively, the data storage may comprise instructions executable by the processor to transmit energy via the transmitter. The received energy may be emitted by a coded material disposed on a drug reservoir, wherein the coded material identifies information related to the drug reservoir. The transmitted energy may be directed at the coded material. The coded material may modify the energy and emit the energy to the receiver of the electronic means. The device may further comprise a display configured to display at least a portion of the information related to the drug reservoir.

According to a first specific embodiment of the drug delivery device, the drug delivery device comprises a drug reservoir holder operable to receive a drug reservoir, electronic means for detecting information related to the drug reservoir. The electronic means comprise a receiver configured to receive electromagnetic radiation emitted from a coded material disposed on the drug reservoir, a processor and data storage. The data storage comprises instructions executable by the processor to determine the information identified by the coded material based upon the received electromagnetic radiation.

According to a further specific embodiment of the drug delivery device, the drug delivery device comprises a drug reservoir holder operable to receive a drug reservoir and an electronic device for detecting information related to the drug reservoir. The electronic device comprises a transmitter configured to transmit energy, a receiver configured to receive energy, a processor and data storage. The data storage comprises instructions executable by the processor to transmit energy via the transmitter, wherein the transmitted energy is directed at the coded material disposed on a drug container, and wherein the coded material modifies the energy and emits the energy to a receiver. Based upon the modified energy received at the receiver, information related to the drug reservoir is determined.

These as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which.

DETAILED DESCRIPTION

The proposed method and system allows for identifying information related to a drug reservoir by an electronic means. The proposed system and method may help a user to distinguish between medicament reservoirs, thereby ensuring that a medical delivery device can only be used with a medicament reservoir for which it is intended. In an arrangement, a given drug delivery device may be intended to only be used with a single drug reservoir. Thus, the proposed system and method may help a user ensure that only the single given drug reservoir is used with the given drug delivery device. However, in other arrangements, a given drug delivery device may be intended for use with multiple drug reservoirs. Thus, the proposed system and method may help a user ensure that only the intended reservoirs are used with the drug delivery device. In addition to allowing a user to identify whether a given drug reservoir is intended to be used with a drug delivery device, the proposed system and method may also inform a user of other useful information regarding a drug reservoir, such as required storage conditions for the reservoir and/or expiration date of the reservoir.

In a first embodiment, information regarding a drug reservoir may be determined by optical detection of a coded material by an electronic means. In a second embodiment, information regarding a drug reservoir may be determined by detecting color of a coded material by an electronic means. These embodiments for identifying information related to a drug reservoir are described in greater detail below.

Figure 1:
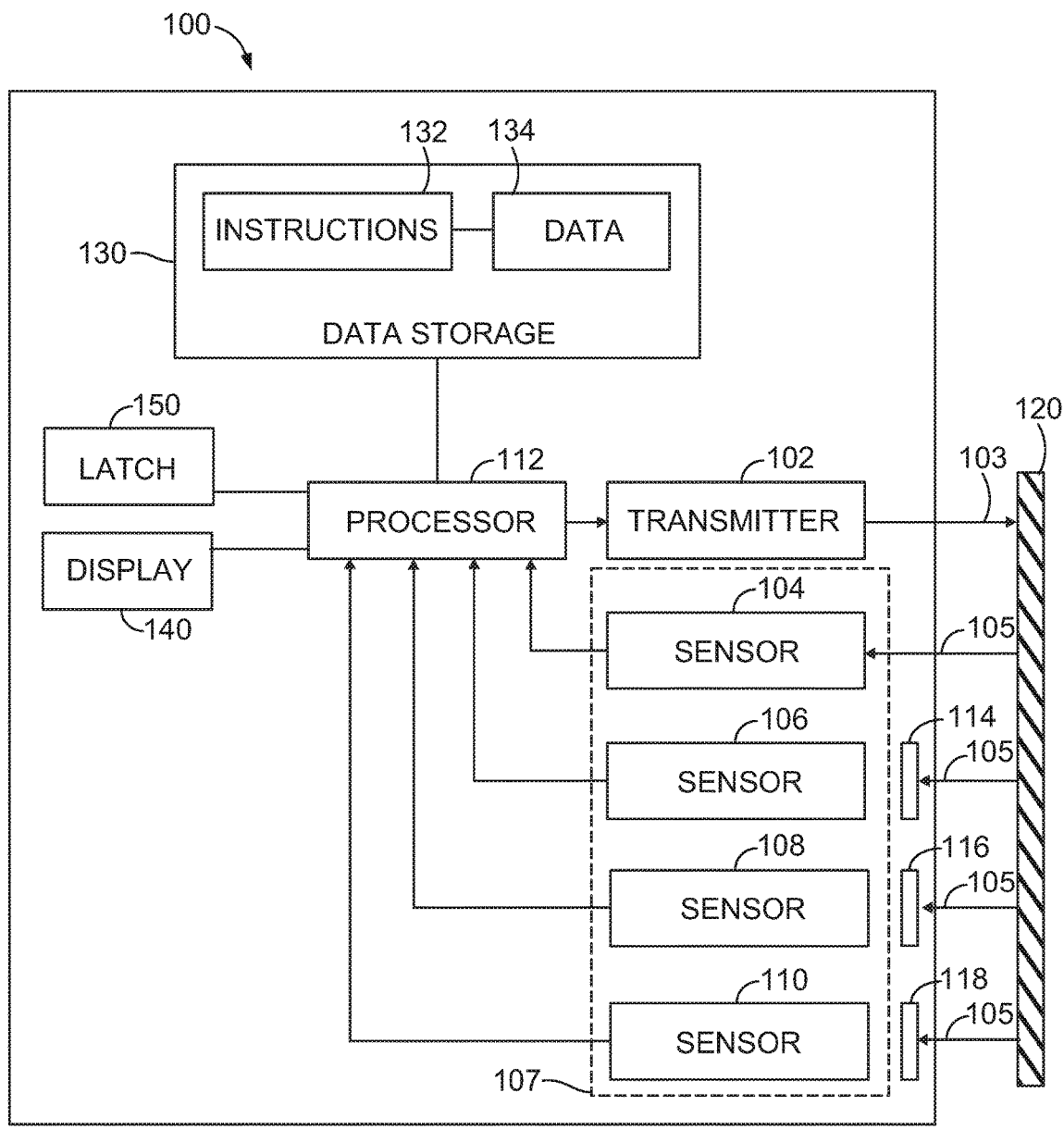
FIG. 1 illustrates a system for optical detection of a coded material that may determine information related to a drug reservoir.

Exemplary Method and System for Identifying Information Related to a Drug Reservoir An Exemplary Architecture FIG. 1 depicts a system 100 for optical detection of a coded material. This system 100 may determine information related to a drug reservoir. System 100 includes transmitter 102, at least one receiver 107, and processor 112. The system may also comprise data storage 130 comprising instructions 132 executable by the processor 112 to carry out the functions described herein. The processor 112 may comprise a single processor such as a general purpose microprocessor or multiple (e.g., parallel) processors. The data storage 130 may take various forms, in one or more parts, such as a non-volatile storage block and/or a removable storage medium, and may include program instructions 132 executable by processor 112 for carrying out the system functions described herein. Data storage 130 may also include data 134, which may be used for carrying out the functions described herein.

An Exemplary Operation

The system 100 may operate to identify information related to a drug reservoir. Specifically, system 100 may operate to identify information related to a drug reservoir by first identifying a coded material, such as coded material 120. As described in greater detail below, the coded material 120 can be applied to a reservoir such as a cartridge, vial, ampoule, pouch, or container. This coded material 120 may serve to indicate information about the drug reservoir the coded material 120 is disposed on. In a preferred embodiment, coded material 120 is disposed on a drug reservoir, such as drug reservoir 400 depicted in FIG. 4.

Figure 9:
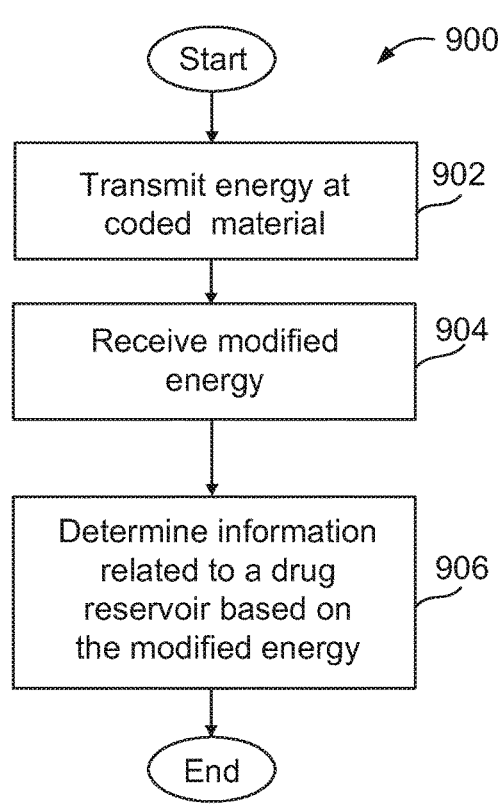
FIG. 9 illustrates an exemplary method of determining information related to a drug reservoir.

FIG. 9 is a flowchart of an exemplary method that may be carried out by system 100, in accordance with an exemplary embodiment. As shown in FIG. 9, method 900 begins at step 902, where system 100 transmits energy at coded material 120, which is preferably disposed on a drug reservoir. The coded material 120 modifies the energy and emits the modified energy to receiver 107. At step 904, receiver 107 receives the modified energy. Then, at step 906, based on the modified energy, system 100 determines information related to the drug reservoir. These steps are further explained in the following subsections.

(a) Transmitting Energy at the Coded Material

In accordance with the proposed method and system, instructions 132 executable by the processor 112 may first cause the transmitter 102 to transmit energy 103. The energy 103 is preferably transmitted at coded material 120, which as described above is preferably disposed on a drug reservoir, such as drug reservoir 400 depicted in FIG. 4. For example, the coded material 120 may be on the reservoir, ferrule, bung, label, connector or an adaptor. However, in other given embodiments, the coded material 120 may be disposed elsewhere, such as on the box of a drug reservoir(s).

The transmitted energy 103 may be any type of energy, such as electromagnetic radiation, and the transmitter may be an LED. The transmitted energy 103 is preferably electromagnetic radiation in the ultra-violet (UV) range. However, the transmitted energy 103 may be electromagnetic energy in other ranges, such as the visible range or infra-red (IR) range. This energy preferably has at least one predefined characteristic, such as a known frequency, duration, and/or known intensity. By having a known predefined characteristic, system 100 will be able to identify a type of coded material 120 based on how the coded material 120 modifies this transmitted energy having a known, predefined characteristic.

(b) Receiving the Modified Energy at the Receiver

After the energy is transmitted at coded material 120, the coded material 120 modifies the energy 103 and emits the modified energy 105 to a receiver 107. This material 120 may be composed of material specifically selected to modify energy in a highly predictable way. As such, the coded material 120 may be composed of various materials or combinations of various materials. For example, coded material 120 may be in the form of volatile chemicals, particles to be identified microscopically, magnetic particles, and/or energy emitting particles, such as fluorescent or phosphorescent materials. At step 904, the receiver 107 receives the modified energy 105.

The receiver 107 may be a single receiver or may include a plurality of receivers, such as sensors 104, 106, 108, 110. The sensors may be, for example, photosensors. For instance, the sensors may be a PIN diode, a phototransistor, a Complementary Metal Oxide Semiconductor (CMOS) sensor (also known as an Active Pixel Sensor (APS)), or a Charge Coupled Device (CCD). Other types of sensors are possible as well.

The receiver 107 may be specifically configured to receive or detect certain information or signals. For example, sensors 104, 106, 108, and 110 may each be configured to detect different information. Further, to aid in detecting different information, other components such as filters 114, 116, and 118 may be placed before certain sensors, such as sensors 106, 108, and 110, respectively.

In an example, sensor 104 may be configured to receive the intensity of modified emitted energy 105, sensor 106 may be configured to receive any light from a first color, sensor 108 may be configured to receive any light from a second color, and sensor 110 may be configured to receive any light from a third color. For example, there may be three filters to detect the colors red, green, and blue light. Color would then be identified by calculating the ratio of light from each sensor. The fourth sensor without a filter could measure the total intensity.

Figure 2A:
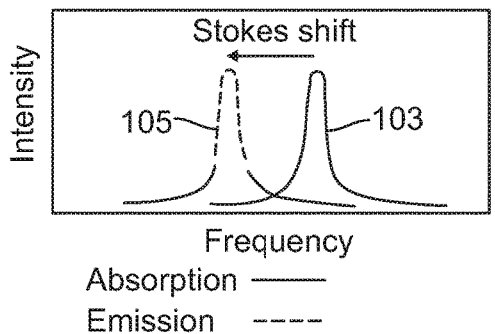
FIGS. 2A-2E illustrate example types of energy modification by a coded material, in accordance with embodiments.
Figure 2B:
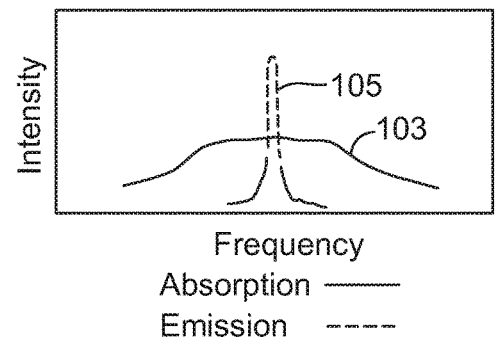

As mentioned above, the coded material 120 may modify the transmitted energy 103 in a variety of ways. FIGS. 2(A)-(B) depict examples of how coded material 120 may modify the transmitted energy. However, it should be understood that these figures are intended to serve as examples of energy modification, and the coded material 120 may modify the energy in additional ways.

With reference to FIG. 2(A), the coded material 120 may cause a frequency shift in the transmitted energy. As depicted in the FIG. 2(A), the energy emission (i.e., the modified energy 105) from the coded material 120 may be at a lower frequency than the absorbed energy (i.e., the transmitted energy 103). This change in frequency is commonly referred to as "down-converting" or a "Stokes shift." In alternative embodiments, the energy emission from the coded material 120 may be at a higher frequency than the absorbed (i.e., transmitted) energy (not depicted). This change in frequency is commonly referred to as "up-converting" or an "anti-Stokes shift." Different types of coded material 120 may cause different frequency shifts.

In other embodiments, the coded material 120 may act as a filter, as depicted by FIG. 2(B). As shown, a narrow band of energy 105 may be returned when the coded material 120 is excited with energy 103 of a broad spectrum. Other examples of filtering are also possible. For instance, a broad spectrum may be returned when the coded material 120 is excited with a narrow band of transmitted energy. Different types of coded material 120 may filter the energy in different ways.

Figure 2C:
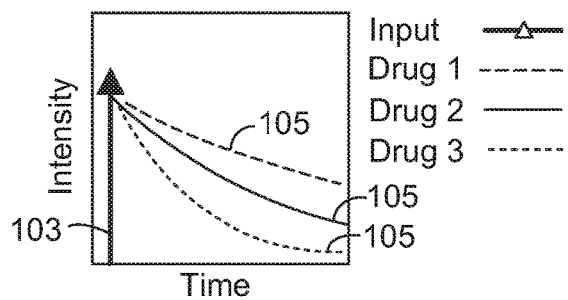

In other embodiments, the coded material 120 may modify the transmitted energy 103 by absorbing the energy 103 and then gradually releasing the energy (e.g., phosphorescence or persistence) with a given rate of decay. An example of such absorption and emission is shown for a plurality of coded materials 120 in FIG. 2(C). Certain coded materials 120 may have a given rate of decay, and decay rates may be chosen from a wide range of rates. For instance, the half-life of a material may vary from nanoseconds to hours. Different types of coded material 120 may have different rates of decay. For example, as depicted, the coded materials 120 for drugs 1-3 have a different rate of decay. Thus, when the receiver 107 detects energy emission at a given rate, the system 100 may determine the type of coded material 120 disposed on the drug reservoir. A mix of phosphorescent materials may be used to control the decay rate of the coded material 120. The materials may preferably be mixed onto the same area of the container; however, each phosphorescent material may be located on a separate area than the other phosphorescent materials.

Figure 2D:
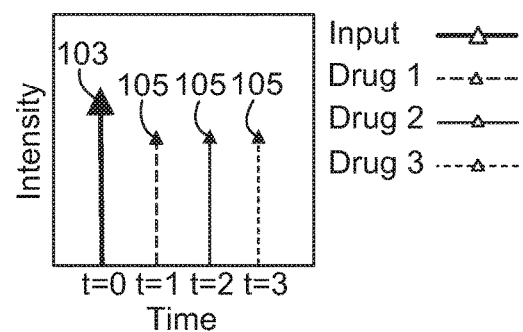

In other embodiments, the coded material 120 may modify the transmitted energy by causing a time shift, as depicted in FIG. 2(D). Coded material 120 may absorb transmitted energy at a give time and emit the energy only after a given delay. Different types of coded material 120 may cause different time shifts. For example, coded material for drug 1 may absorb transmitted energy at t=0 and emit the energy at t=1, coded material for drug 2 may absorb transmitted energy at t=0 and emit the energy at t=2, and coded material for drug 3 may absorb transmitted energy at t=0 and emit the energy at t=3.

Figure 2E:
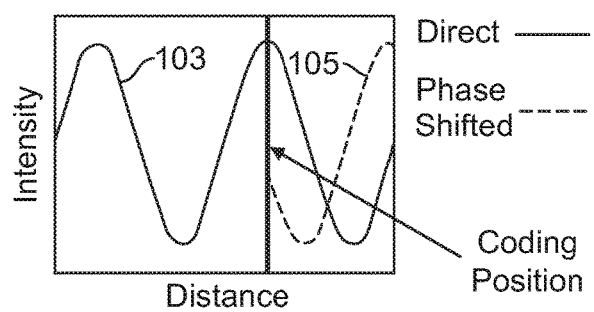

Further, the coded material 120 may modify the transmitted energy by causing a phase shift, as depicted in FIG. 2(E). Different types of coded material 120 may cause different phase shifts. Other types of energy modification by the coded material 120 are possible as well.

In order to accurately identify the coded material 120, the receiver 107 must be able to distinguish between the transmitted energy 103 (illumination) and the energy 105 modified by the coded material 120. For various reasons (e.g. losses in the material, or scattering of light), the receiver 107 may detect the illumination 103 with higher intensity than the modified energy 105, so the modified energy 105 may be difficult to detect. To alleviate this problem, in one embodiment, optical filters may be used to filter out the illumination. Alternatively, if the coded material 120 delays the release of energy (phosphoresence), the illumination 103 may be applied for a pulse, and then the response detected after the illumination 103 is switched off. In another embodiment, if the coded material 120 uses a frequency shift (fluorescence), down-converting the frequency makes it easier to distinguish the modified energy 105 from the illumination 103. Optical sensors are generally most sensitive to IR, and the response reduces through higher frequencies (visible and then UV). So, in a system such as system 100 that uses high frequency illumination (e.g., UV) and when lower frequencies emitted by the coding material 120 (e.g., visible), the coding is easy to distinguish from the illumination 103.

In another embodiment, the effects of ambient light may be filtered out electronically. For example, the system 100 may be programmed to read for ambient light before the illumination 103 (i.e., transmitted energy) is turned on. Additionally or alternatively, the system 100 may be programmed to read for ambient light after the response has decayed sufficiently.

Since the coded material 120 may modify the transmitted energy 103 in a predictable way, system 100 may determine what type of coded material 120 is disposed on the drug reservoir 400 based on the received energy 105. Different coded materials 120 will modify the transmitted energy 103 in different ways. Therefore, based on the modified energy 105, system 100 may identify the coded material 120.

(c) Determining Information Related to the Drug Reservoir

Based on this modified energy 105, the system 100 determines information related to the drug reservoir. As described above, the system 100 is able to determine information related to the drug reservoir based on modified energy 105 because the coded material 120 may modify the transmitted energy 103 in a predictable way. Based on the identified coded material 120, system 100 may identify information related to the drug reservoir. For instance, coded material 120 may vary for different types of drug reservoirs. As a particular example, a first given coded material 120 may be associated with a first drug reservoir and may modify the transmitted energy 103 in a first way. A second given coded material 120 may be associated with a second drug and may modify the transmitted energy 103 in a second way. Further, a third coded material 120 may be associated with a third drug reservoir, and so forth.

As a particular example, if the received modified energy 105 detected by system 100 indicates that the energy 103 was modified in the first way, system 100 may determine that the drug reservoir is the first drug reservoir. However, if the received modified energy indicates that the energy was modified in the second way, the system may determine that the drug reservoir is the second drug reservoir.

As discussed above, system 100 may comprise data storage 130 that includes data 134. This data 134 may comprise a database of information that links a plurality of coded materials 120 to respective information regarding a given drug reservoir. For example, the database may include information that links a given coded material 120 to a type of drug the drug reservoir contains. In addition to identifying a type of drug or drug reservoir, the coded material 120 may serve to identify other information about a drug reservoir. For example, the information related to the drug reservoir may be information related to drug type, a drug concentration, a manufacturing date of the reservoir, an expiration date of the drug, and a storage condition of the drug (e.g., required storage temperature). Other types of information about a drug reservoir are possible as well.

Figure 3A:
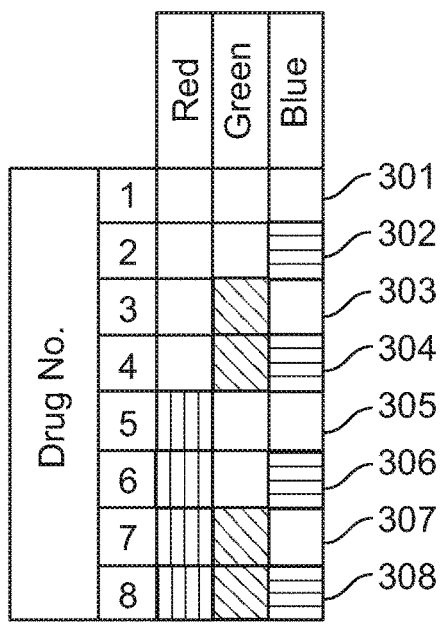
FIGS. 3A and 3B illustrate examples of possible combinations for coded materials, in accordance with embodiments.

In accordance with the proposed method and system, a large amount of information may be coded (e.g., distinguishing a large number of medicament reservoirs) by varying the coded material or coding features disposed on the drug reservoir. For instance, multiple materials may be provided in order to provide coding for drug reservoirs. The multiple materials may be configured to emit energy, for example electromagnetic radiation, wherein the energy from the multiple materials may differ in at least one predefined characteristic. The determined information may comprise information based on the differing predefined characteristics. For example, three coded materials may be provided that each fluoresce to a different color. Based on these three different materials, there may be eight ($2^3$) possible combinations that may each define given information about a drug reservoir (e.g., eight different types of drug reservoirs). An example of eight possible combinations 301-308 using three different materials is shown in FIG. 3(A). As shown, each combination may serve to identify a different drug (i.e., Drug Nos. 1-8). It should be understood that many more combinations are possible by, for instance, using four or more coded materials. In the above example, it is assumed that the sensors can only detect the presence (or absence) of each color. If the sensors can detect the ratio of each color, far more combinations could be distinguished.

In some embodiments, the position of the coded material 120 may also be used for identification purposes. For example, position of the coded material 120 relative to a standard feature may be used to identify information about the drug reservoir. As such, system 100 may be further configured to detect the position of the coded material 120.

Figure 4A:
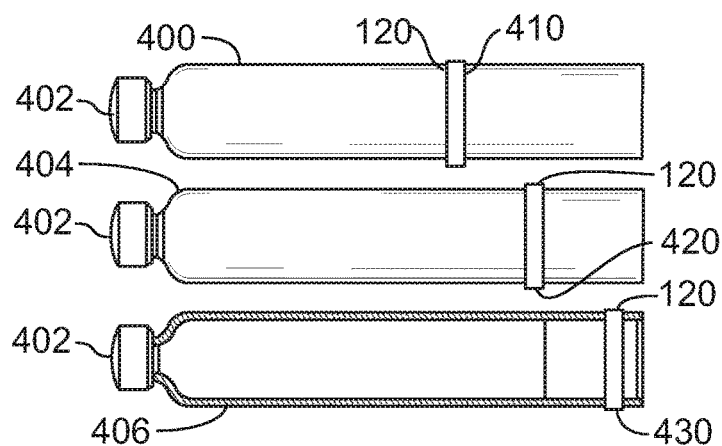
FIGS. 4A and 4B illustrate examples of possible positions of coded material on a drug reservoir, in accordance with embodiments.
Figure 4B:
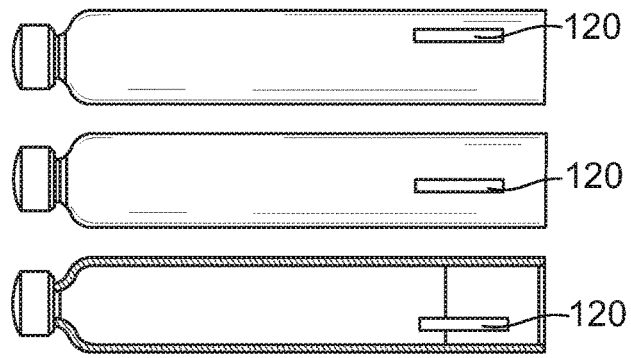

As an example, with reference to FIG. 4(A), system 100 may be configured to detect the position of the coded material 120 relative to the axial length from the distal end 402 of the drug reservoir 400. For instance, coded material 120 at position 410 may indicate to system 100 that the drug reservoir is reservoir 400; coded material 120 at position 420 may indicate to system 100 that the drug reservoir is reservoir 404; and coded material 120 at position 430 may indicate to system 100 that the drug reservoir is reservoir 406. If position is used for the coding, the position on different drugs is preferably far enough apart (e.g., 10 millimeters (mm)) so that the drugs may be accurately distinguished from one another.

In alternative embodiments, the system 100 may identify a coded material 120 based on the size (e.g., the axial, circumferential, and/or radial extent of the coded material 120) or orientation (e.g., axial strips, circumferential rings, or 2D pattern) of the coded material 120.

The coded material 120 is preferably non-visible, e.g. UV or IR radiation. Therefore, the coded material 120 may not aesthetically affect the drug reservoir, and allow for covert coding; however, the system 100 would still be capable of identifying the drug reservoir based on the non-visible coded material 120. It should be understood, however, that the coded material 120 may be visible.

An Exemplary Drug Delivery Device

In accordance with the disclosed system and method, system 100 may be provided on or in a drug delivery device, such as syringes, pen-type injection syringes, credit-card-shaped injection devices, pumps, inhalers, or other similar injection or infusing devices that require at least one reservoir containing at least one medicament. For example, system 100 may be provided in pen type drug delivery device 600 shown in FIG. 6. The drug delivery device 600 comprises a housing 602 having a first cartridge retaining part 604, and second main (exterior) housing part 606 that includes a dose setting mechanism. A first end of the cartridge retaining means 604 and a second end of the main housing 606 are secured together by retaining features 608. In this illustrated arrangement, the cartridge retaining means 604 is secured within the second end of the main housing 606. The pen type syringe may comprise a re-usable or a disposable pen type syringe. Where the syringe comprises a re-usable device, the cartridge holder 604 and the dose setting mechanism are removably coupled together. In a disposable device, they may be permanently coupled together.

A drug reservoir such as drug reservoir 400, from which a number of doses of a medicinal product may be dispensed, may be inserted in the cartridge retaining part 604. Preferably, the drug reservoir 400 contains a type of medicament that must be administered often, such as once or more times a day. One such medicament is insulin.

In an embodiment, the system 100 is provided at or near the interface between the cartridge retaining part 604, and main housing part 606. Thus, when a drug reservoir 400 is inserted in the drug delivery device 600, the system 100 may detect information related to the reservoir 400being inserted.

Since information regarding the drug reservoir 400 may be detected during or after a drug reservoir 400 is inserted into a drug delivery device 600, the method and system may react to the identified information at various stages in an operating sequence of the drug delivery device 600. Specifically, system 100 may be configured to take certain actions when a drug reservoir 400 is identified. For instance, the system 100 may react to the information and take an appropriate action during (i) loading of the device, (ii) dose selection, and (iii) dispensing of the drug. Other stages are possible as well. Beneficially, during these steps, the system 100 may help a user identify whether the drug reservoir 400 being loaded or that is loaded is intended for the drug delivery device 600.

The step of determining information related to the drug reservoir 400 may be performed as a user loads the drug reservoir 400 in drug delivery device 600. System 100 may identify the coded material 120 and then may determine, based on the coded material 120, whether the drug reservoir 400 is intended for use with the drug delivery device 600.

In an embodiment, when the drug reservoir 400 is not intended for use with the drug delivery device 600, the system 100 may display an indication that the drug reservoir 400 is not intended for use with the drug delivery device 600. For instance, as shown in FIG. 1, the system 100 may comprise a display feature 140 that is in communication with the processor 112. This display feature 140 could indicate that the drug reservoir 400 is incorrect. For example, the display feature may display a red dot or red "X" when an incorrect drug reservoir is loaded. The display feature 400 may also operate to indicate when a correct drug reservoir 400 is loaded. For example, the display feature 140 may display a green dot when a correct drug reservoir 400 is loaded. Other types of indications are possible as well, such as an audible indication.

If a user attempts to insert an incorrect reservoir 400 into the drug delivery device 600, the system 100 may operate to prevent the insertion of the drug reservoir 400 into the drug delivery device 600. For instance, preventing insertion of the drug reservoir 400 may comprise activating an electronically-controlled latch, such as latch 150 shown in FIG. 1, which prevents insertion of the drug reservoir 400. System 100 may also be configured to prevent the reset of a piston rod of the drug delivery device 600 with an incorrect drug container 400.

In an embodiment, system 100 may be configured to block the insertion of all drug reservoirs other than a given drug reservoir for which the drug delivery device is intended. In another embodiment, the system may be configured to only block drugs that are considered dangerous for using with the device (e.g., a short-acting drug could be fitted into a device intended for long-acting insulin, or a low-concentration drug could be fitted into a device intended for a high-concentration drug, but not vice versa).

The method and system may also react to an identified drug reservoir and take an appropriate action during a dose selection phase (i.e., when a user is selecting a dose). For instance, system 100 may be configured to control dose selection based on the identified drug reservoir. Similar to preventing loading of an incorrect drug reservoir, system 100 may be configured to prevent dose selection when the identified drug reservoir is not intended for use with the drug delivery device. System 100 may, for instance, trigger a latch, such as latch 150 that prevents a user from setting a dose when an incorrect reservoir is loaded in the drug delivery device.

Other examples of controlling dose selection are possible as well. For instance, system 100 may control dose selection based on the identified drug reservoir by setting or enforcing a maximum dose. The drug reservoir may contain a drug that should only be dosed in small increments (e.g., 20 units or less). Thus, the system 100 may be configured to prevent a user from setting a dose greater than 20 units when such a drug reservoir is inserted in the drug delivery device. As another example, system 100 may control dose selection based on the identified drug reservoir by setting or enforcing a minimum dose.

As yet another example, system 100 may control dose selection based on the identified drug reservoir by controlling the dosing frequency. For instance, if a drug should not be dosed more than once a day, after a user injects a dose, the system 100 may be configured to lock the drug delivery dose setting mechanism out for a 24-hour period. For example, the system 100 may activate the electronic latch 150 to prevent dose setting for the 24-hour period.

The method and system may also react and take an appropriate action during the dispensing phase (i.e., when a user dispenses the drug). The system 100 may be configured to control dispensing of the drug based on the identified drug reservoir. For example, similar to preventing loading of an incorrect drug reservoir and dose selection with an incorrect reservoir, system 100 may be configured to prevent dispensing when the identified drug reservoir is not intended for use with the drug delivery device.

As another example, controlling dispensing of the drug based on the identified drug reservoir may include controlling a dispense speed and/or a required dispense force. Controlling a dispense speed and/or a required dispense force may be beneficial for various reasons. For example, certain drugs may require an increased dispense force due to crystallizing on the bung and/or high viscosity. In such a case, it may be beneficial to inject the drug slowly in order to reduce the force needed by a motorized drive. Further, in such a case, injecting such a drug may be painful for the user, so slower injection may reduce any pain. As another example, one other reason to control speed/force is to detect abuse loads, e.g. to detect blockages it is necessary to know what force is 'normal' for a given drug at a given speed.

As yet another example of identifying information related to a drug reservoir, system 100 may be used to identify the time that has elapsed since a drug reservoir was loaded into a drug delivery device. For example, the time at which the cartridge holder latch was last operated could be recorded into memory in the device, or on the drug reservoir.

Alternatively, rather than system 100 being disposed in or on a drug delivery device, system 100 may be a stand-alone device, such as a scan gun or used for identifying information related to drug reservoirs or a drug-identification base station. The stand-alone system may be used by, for example, a patient or medical staff personnel, or a drug manufacturer in order to identify information related to drug reservoirs. Such a stand-alone device may be used for a variety of reasons. For example, the stand-alone system may be used to aid with storage or shipping of drug reservoirs. As a particular example, the system 100 may be used to identify the expiration date of the drug reservoir. As another example, system 100 may be used to identify required storage conditions for the drug reservoir. It may also be possible to record storage conditions experienced by a cartridge, e.g. with a temperature sensitive label, and for this information to be read by the device.

Figure 5A:
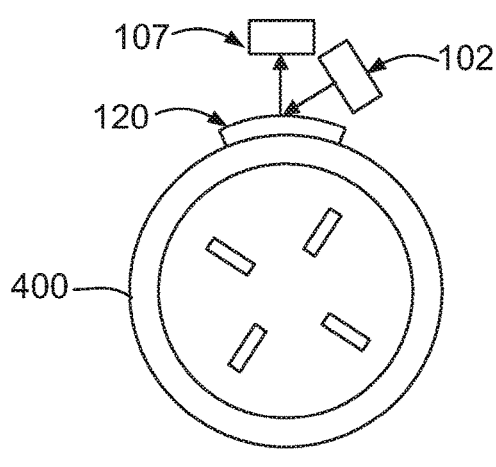
FIGS. 5A and 5B illustrate examples of possible arrangements of a transmitter and receiver of the system depicted in FIG. 1, in accordance with embodiments.
Figure 5B:
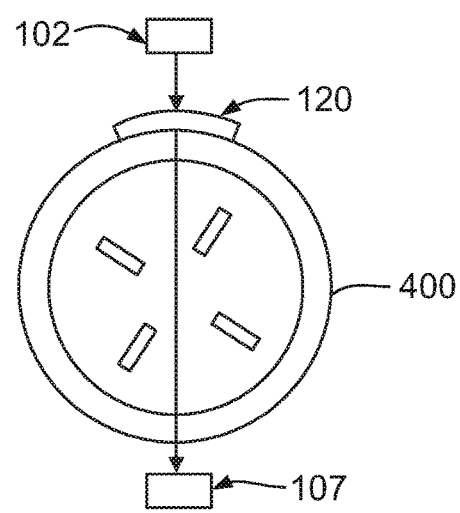

The transmitter 102 and receiver 107 of system 100 may be arranged in various ways in order to transmit the energy 103 at a coded material 120 and receive the emitted energy 105 at the receiver 107. For instance, transmitter 102 and receiver 107 may be adjacent to one another. For example, the transmitter 102 and receiver 107 may be arranged as shown in FIG. 5(A). The transmitter 102 and receiver 107 may be at any angle in a transverse or longitudinal plane, but the receiver 107 would preferably be normal to the surface of the container. Alternatively, the transmitter 102 and receiver 107 may be on opposite sides of the drug reservoir 400, as shown in FIG. 5(B). If the coded material 120 is located on a curved surface, and if the surface is misaligned relative to the transmitter 102 and receiver 107, the modified energy 105 might not be transmitted towards the receiver 107. To resolve this potential issue, the coded material 120 may be provided on a flat surface of the drug reservoir 400, such as on an adaptor.

In an embodiment, the coded material 120 may be applied around the full circumference of the drug reservoir 400. For example, as shown in FIG. 4(A), coded material 120 is applied around the full circumference of drug reservoir 400. In such an embodiment, the orientation of the drug reservoir 400 as it is loaded is not important. In other arrangements, the coded material 120 may be a discrete area, (e.g. a strip) of material that is not disposed around the full circumference of a reservoir 400, such as the strips of coded material 120 shown in FIG. 4(B).

In an alternative embodiment, the coded material 120 may be aligned with the receiver(s) of system 100 when a drug reservoir 400 is loaded. Alignment may be accomplished in various manners, such as aligning the coded material 120 with the receiver of system 100 using a mechanical protrusion or indentation in the drug reservoir 400 to force alignment.

In an embodiment, where multiple areas of coding are applied, the multiple areas of coding may be read during insertion into the reading apparatus, so that only one receiver 107 is needed. For example, a reservoir 400 may have three areas of coding, such as a coded area indicating a storage condition, a coded area indicating the type of drug, and a coded area indicating expiration date. These coded areas may be displaced vertically 5 mm apart from one another. As a drug reservoir is inserted into the system, the system may scan the coded areas at each 5 mm interval and may identify all three coded materials 120.

It should be understood that the functional and structural properties described above are not limited to the system as shown in FIGS. 1 and 9. In particular, any of the disclosed methods and drug delivery devices may comprise any of these properties and any combination of these properties.

Figure 7:
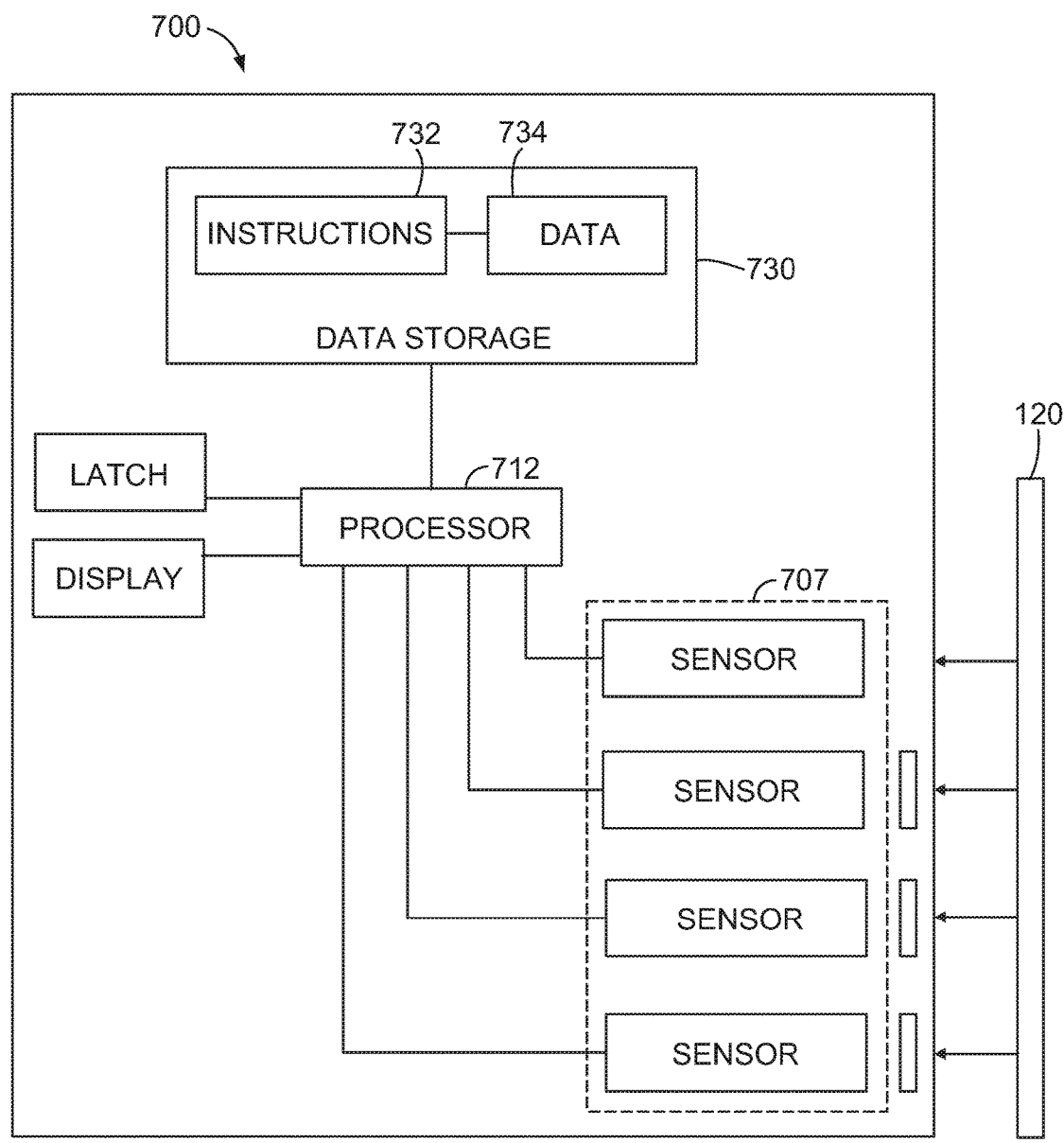
FIG. 7 illustrates a system for detecting color of a coded material that may determine information related to a drug reservoir.

Another Exemplary Method and System for Identifying Information Related to a Drug Reservoir As mentioned above, in another embodiment, information regarding a drug reservoir may be determined by detecting color of a coded material 120 by an electronic means. FIG. 7 illustrates a system 700 for detecting color of a coded material 120. Thereby, this system 700 may determine information related to a drug reservoir. System 700 includes at least one receiver 707 and processor 712. The system may also comprise data storage 730 comprising instructions 732 executable by the processor 712 to carry out the identification functions described herein. The data storage 730 may take various forms, in one or more parts, such as a non-volatile storage block and/or a removable storage medium, and may include (a) program instructions 732 executable by processor 712 for carrying out the system functions described herein and (b) data 734. In an embodiment, to improve accuracy of system 700, the system 700 may include a transmitter that illuminates the colored areas by light of a known frequency or intensity.

This system 700 detects colors in a similar fashion to system 100 as described above. Furthermore, system 700 is related in some respects to system 100, and thus is not described in as great of detail. It should be explicitly noted, however, that many possibilities and permutations described above with respect to system 100 may equally apply to system 700. However, rather than transmitting energy at the coded material 120 and detecting emitted energy, the system 700 is configured to detect the color of the coded material 120. In certain embodiments, however, a transmitter, such as the transmitter 102 illustrated in FIG. 1 and described above, may be used to illuminate the coded material 120.

Figure 10:
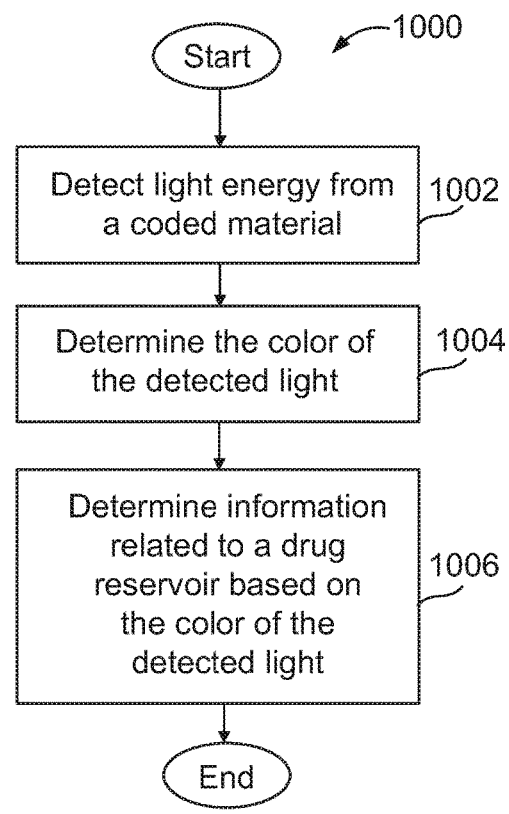
FIG. 10 illustrates an exemplary method of determining information related to a drug reservoir.

Further, FIG. 10 is a flowchart of an exemplary method that may be carried out by system 700, in accordance with an exemplary embodiment. As shown in FIG. 10, method 1000 begins at step 1002, where system 700 detects light energy from a coded material, such as coded material 120, which is preferably disposed on a drug reservoir. The coded material 120 comprises a material having at least one color. At step 1004, the color of the detected light energy is determined. Then, at step 1006, based on the color of the detected light energy, information related to the drug reservoir is determined by system 700.

Figure 3B:
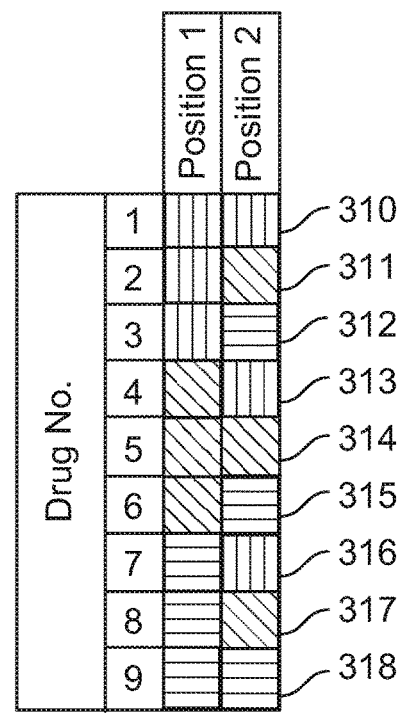

Beneficially, a large amount of information may be distinguished by using color codes. For example, referring to FIG. 3(B), if there are two colored areas on a drug reservoir and each colored area can be one of three colors, there are nine possible combinations, 310-318. It should be appreciated that more combinations of color codes are possible by increasing the number of colored areas and/or the number of possible colors. Further, given that many drug reservoirs are already color-coded reservoirs, this proposed method 1000 and system 700 beneficially avoids the need for additional coding on a drug delivery device. That is, system 700 may be used for drug reservoirs as currently manufactured, without the need to add an additional coding material to the reservoirs.

It should be understood that the functional and structural properties described above are not limited to the system and method as shown in FIGS. 7 and 10. In particular, any of the disclosed methods and drug delivery devices may comprise any of these properties and any combination of these properties.

The disclosed concepts result in a number of advantages. For example, the disclosed concept may result in a user-friendly system that identifies information related to a drug reservoir automatically by electronic means. More, there are quite a large number of different coding materials that may be used. Consequently, with the disclosed coding scheme, a large number of medicaments can be distinguished from one another. Moreover, with the disclosed coding scheme, if a user attempts to load an incorrect reservoir, the user may be alerted at an early stage of the assembly step that the user is attempting to load in incorrect reservoir, and hence attempting to possibly use a wrong medicament.

Additionally, the proposed system and method may make drug reservoirs difficult to counterfeit. The proposed system and method may beneficially reduce tampering and/or counterfeiting of drug reservoirs. Because such reservoirs with coded materials may be difficult to tamper with, they may also reduce the risk of counterfeiting: i.e., making it more difficult for counterfeiters to provide unregulated counterfeit medicament carrying products.

An additional benefit is that an electrical connection is not needed to the drug delivery device, making it easy to use and portable, etc.

Figure 6:
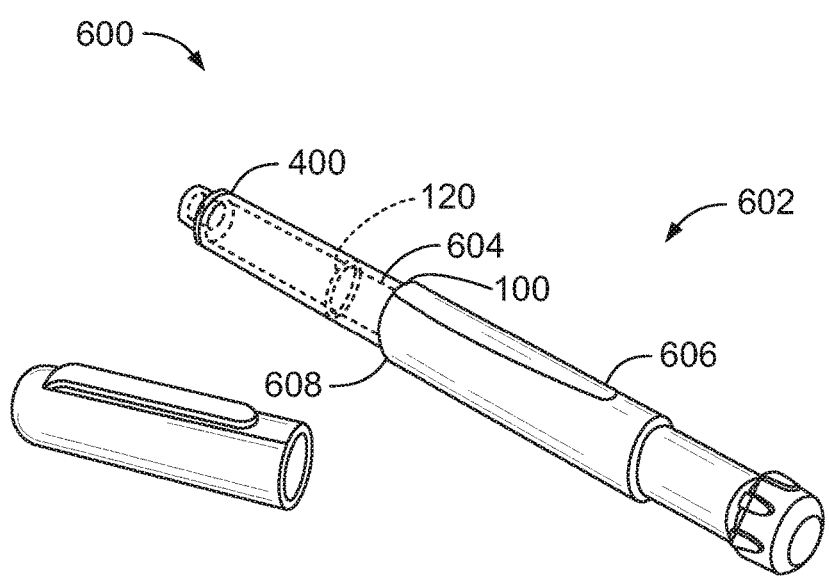
FIG. 6 illustrates a typical pen type drug delivery device that may include the system of FIG. 1.

Although aimed primarily at the insulin market, the invention may apply to other drugs. The disclosed method and system may apply to various devices, including the following examples; an injector pen with a cartridge (e.g. 3 ml cylindrical glass cartridge) and a separate holder as illustrated in FIG. 6. Applicant's present application may also apply to an injector pen with a cartridge (e.g. 3 ml cylindrical glass cartridge) non removably retained in a holder, so that the holder will be disposed of with the primary pack, and to an injector pen where the primary pack attaches directly to the pen, e.g. an injection moulded polymer cartridge.

Figure 8:
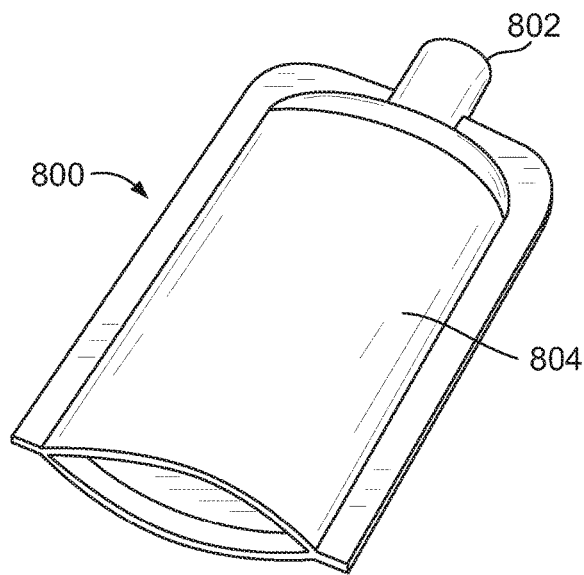
FIG. 8 illustrates an alternative reservoir that may be used in accordance with embodiments of the proposed system and method.

In other applications, the disclosed method and concept may apply to any drug delivery device, with any type of primary pack, e.g. inhaler, pouch. For example, coding features such as a coded material 120 may be added to a pouch, such as the pouch 800 illustrated in FIG. 8. In an embodiment, coding features are added to port 802. However, coded material 120 may also be added to the body 804 of the pouch 800.

Figure 11:
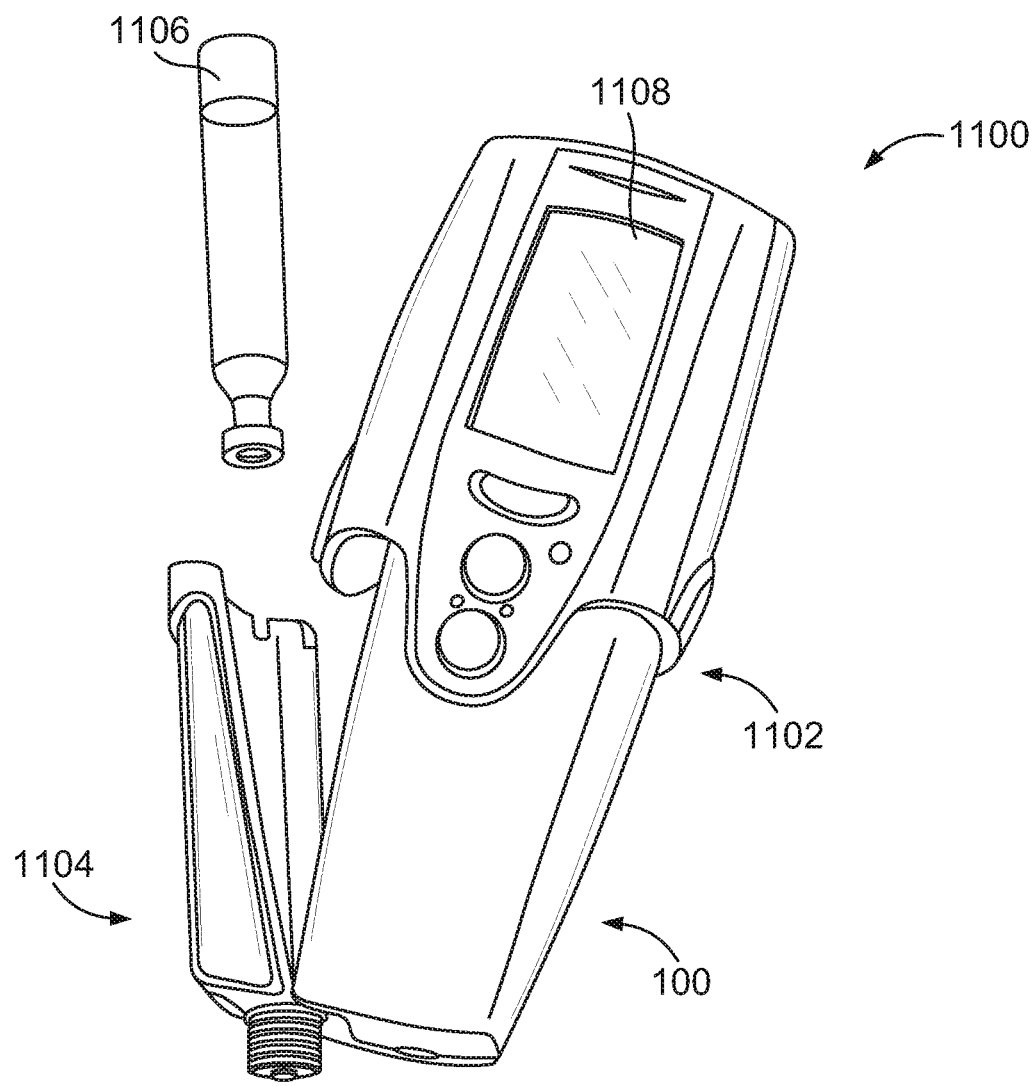
FIG. 11 illustrates another drug delivery device that may include the system of FIG. 1.

Another example of a device that may include system 100 or system 700 is shown in FIG. 11. System 100 or system 700 may be provided in drug delivery device 1100 shown in FIG. 11. Referring to FIG. 11, there is shown a drug delivery device 1100, which is a credit-card-shaped drug delivery device. Drug delivery device 1100 comprises a body 1102. Body 1102 includes a cartridge retaining portion 1104 into which a cartridge 1106 may be inserted. When cartridge 1106 is inserted, system 100 may detect information related to the cartridge. Device 1100 also includes a screen 1108, which may display information related to the cartridge 1106 to the user of the device 1100. It should be understood that systems 100 and 700 may be used in various other devices as well.

Exemplary embodiments of the present invention have been described. Those skilled in the art will understand, however, that changes and modifications may be made to these arrangements without departing from the true scope and spirit of the present invention, which is defined by the claims.

The invention claimed is:

1. A method of determining information related to a drug reservoir, the method comprising:
   providing a drug reservoir comprising a coded material, wherein the coded material identifies information related to the drug reservoir;
   providing electronic means for determining the information, wherein the electronic means comprise a receiver;
   partially inserting the drug reservoir into a drug reservoir holder of a drug delivery device such that the coded material is positioned within the drug reservoir holder so that electromagnetic radiation emitted from the coded material is received by the receiver;
   receiving by the receiver electromagnetic radiation emitted from the coded material;
   based on the received electromagnetic radiation, determining the information identified by the coded material;
   based on the determined information, determining whether the drug reservoir is intended for use with the drug delivery device;
   if the determination is that the drug reservoir is not intended for use with the drug delivery device, then preventing complete insertion of the drug reservoir into the drug reservoir holder by activating an electronically-controlled latch and displaying an indication to a user of the drug delivery device that the drug reservoir is incorrect by means of a display operable to provide an indication to a user of the drug delivery device whether the drug reservoir is intended for use with the drug delivery device; and
   if the determination is that the drug reservoir is intended for use with the drug delivery device, then (i) controlling dose selection based on the identified drug reservoir, and (ii) controlling a dispensing operation of the drug based on the identified drug reservoir,
   wherein the step of determining information related to the drug reservoir is performed while the drug reservoir is positioned at least partially within the drug reservoir holder of the drug delivery device.

2. The method of claim 1, wherein the electronic means comprise a transmitter for transmitting electromagnetic radiation, the method further comprising:
   transmitting electromagnetic radiation by the transmitter to the coded material,
   wherein the radiation has at least one predefined characteristic and wherein the coded material modifies the characteristic of the radiation and emits the modified radiation to the receiver,
   wherein the information determined is based on the received modified radiation.

3. The method of claim 2, wherein the coded material modifies the electromagnetic radiation by at least one of shifting the frequency of the transmitted radiation, filtering the radiation, absorbing the transmitted radiation followed by gradually releasing the radiation, absorbing the transmitted radiation followed by releasing the radiation after a given delay, and shifting the phase of the transmitted radiation.

4. The method of claim 1, wherein controlling dose selection based on the identified drug reservoir comprises at least one of the following steps:
   a) setting a maximum dose of drug for a dispensing operation of the drug delivery device;
   b) setting a minimum dose of drug for a dispensing operation of the drug delivery device;
   c) controlling the dosing frequency for a dispensing operation of the drug delivery device.

5. The method of claim 1, wherein controlling a dispensing operation of the drug based on the identified drug reservoir comprises at least one of the following steps:
   a) controlling a dispense speed for dispensing a drug retained in the drug reservoir;
   b) controlling a required dispense force for dispensing a drug retained in the drug reservoir.

6. The method of claim 1, wherein the coded material comprises material having at least one color and wherein the method further comprises:
   receiving by the receiver light from the coded material, determining by the electronic means the color of the received light and based on the color of the received light determining information related to the drug reservoir.

7. A drug delivery device comprising:
   a drug reservoir holder operable to receive a drug reservoir;
   an electronically controlled latch, which, when activated, is configured to prevent complete insertion of the drug reservoir into the drug reservoir holder;
   electronic means for detecting information related to the drug reservoir, the electronic means comprising:
   a receiver configured to receive electromagnetic radiation emitted from a coded material disposed on the drug reservoir, where the receiver is positioned relative to the drug reservoir holder so that the emitted electromagnetic radiation is received when the drug reservoir is being inserted into the drug reservoir holder;
   a display operable to provide an indication to a user of the drug delivery device whether the drug reservoir is intended for use with the drug delivery device;
   a processor; and data storage comprising instructions executable by the processor to:

based upon the electromagnetic radiation received by the receiver during insertion of the drug reservoir into drug reservoir holder, determine the information identified by the coded material; and based on the determined information, determining whether the drug reservoir is intended for use with the drug delivery device;

if the determination is that the drug reservoir is not intended for use with the drug delivery device, then activating the electronically controlled latch to thereby prevent complete insertion of the drug reservoir into the drug reservoir holder and displaying an indication to the user of the drug delivery device that the drug reservoir is incorrect; and if the determination is that the drug reservoir is intended for use with the drug delivery device, then (i) controlling dose selection based on the identified drug reservoir, and (ii) controlling a dispensing operation of the drug based on the identified drug reservoir.

8. The drug delivery device of claim 7, further comprising:

a transmitter configured to transmit electromagnetic radiation to be directed at the coded material, wherein the electronic means are configured to be used with a coded material which modifies the transmitted radiation, wherein the receiver is configured to receive the modified radiation and wherein the processor is configured to determine information based upon the modified radiation.

9. The drug delivery device of claim 7, wherein the processor is configured to execute or trigger executing at least one of the method steps of claim 1.

10. The drug delivery device of claim 7, configured to be used with the coded material comprising at least one of a volatile chemical, a particle to be identified microscopically, a magnetic particle, a fluorescent material, and a phosphorescent material.

11. The drug delivery device of claim 7, configured to be used with the coded material comprising multiple coded materials emitting electromagnetic radiation, wherein the electromagnetic radiation from the multiple coded materials differ in at least one predefined characteristic and wherein the determined information comprises information based on the differing predefined characteristics.

12. The drug delivery device of claim 7, configured to be used with a non-visible coded material.

13. The drug delivery device of claim 7 having at least one of the following designs:

a) The transmitter is an LED;

b) The receiver comprises at least one photosensor.

14. A method of determining information related to a drug reservoir, the method comprising:

providing a drug reservoir comprising a coded material, wherein the coded material identifies information related to the drug reservoir;

providing electronic means for determining the information, wherein the electronic means comprise a receiver that is positioned relative to a drug reservoir holder of a drug delivery device such that the receiver can receive electromagnetic radiation emitted from the coded material;

partially inserting the drug reservoir into the drug reservoir holder such that the coded material is positioned within the drug reservoir holder so that the electromagnetic radiation emitted from the coded material is received by the receiver;

receiving by the receiver the electromagnetic radiation emitted from the coded material; and based on the received electromagnetic radiation, determining the information identified by the coded material, and based on the determined information, determining whether the drug reservoir is intended for use with a drug delivery device and, if it is not, informing a user of the drug delivery device that the drug reservoir is incorrect and preventing the user for a predetermined time period from setting a dose on the drug delivery device and preventing complete insertion of the drug reservoir into the drug reservoir holder by triggering an electronically-controlled latch, wherein the step of determining information related to the drug reservoir is performed while the drug reservoir is positioned at least partially within the drug reservoir holder.

* * * * *